United States Patent
Suzuki et al.

[11] Patent Number: 6,057,484
[45] Date of Patent: May 2, 2000

[54] METHOD OF OBTAINING A COMPOSITION CONTAINING 9-CIS β-CAROTENE IN HIGH-PURITY

[75] Inventors: Takehiko Suzuki; Nobuko Ohishi; Kunio Yagi, all of Aichi-ken, Japan

[73] Assignee: Institute of Applied Biochemistry, Mitake-cho, Japan

[21] Appl. No.: 09/047,346

[22] Filed: Mar. 25, 1998

[30] Foreign Application Priority Data

Dec. 26, 1997 [JP] Japan ................... P9-359798

[51] Int. Cl.⁷ .................................. C07C 403/00
[52] U.S. Cl. ............................................. 585/351
[58] Field of Search ............................................. 585/351

[56] References Cited

U.S. PATENT DOCUMENTS

| | | | |
|---|---|---|---|
| 4,439,629 | 3/1984 | Rüegg | 585/803 |
| 5,310,554 | 5/1994 | Haigh | 424/439 |
| 5,612,485 | 3/1997 | Schlipalius | 585/351 |

OTHER PUBLICATIONS

Pharmaceutical Biotechnology, vol. 3, pp. 34–39, Yuan et al., 1996–no month.
Biochemistry Molecular Biology International, vol. 39, pp. 1077–1084, Suzuki et al., 1996–Aug.
J. Amer. Chem. Soc., vol. 64, pp. 1856–1861, Polgar et al., 1942–no Aug.

*Primary Examiner*—Walter D. Griffin
*Assistant Examiner*—Nadine Preisch
*Attorney, Agent, or Firm*—Arent Fox Kintner; Plotkin & Kahn, PLLC

[57] ABSTRACT

There are disclosed a composition containing 9-cis β-carotene in high-purity and an industrially applicable method of obtaining the same from an alga. The composition can be obtained through steps of washing with ethanol dry powder of the alga belonging to Dunaliella, adding hexane to the washed algal powder, stirring the same, subjecting the same to filtration to obtain a filtrate, concentrating the filtrate to obtain a semi-solidic concentrate, adding hexane to the semi-solidic concentrate in an amount of 10–18 ml of hexane to 1 g of the semi-solidic concentrate, stirring the same, subjecting the same to filtration to obtain a filtrate, concentrating the filtrate to obtain an oily concentrate, adding hexane to the oily concentrate in an amount of 2–4.5 ml of hexane to 1 g of the oily concentrate to dissolve the same, and leaving the solution, as it is, under lower temperature condition to cause a separation of the composition. The composition is a rubiginous powder or crystals and contains 9-cis β-carotene in an amount of 75% or more to total amount of the composition.

6 Claims, 1 Drawing Sheet

Peak 1 : α-Carotene
Peak 2 : Unknown carotene
Peak 3 : All-trans β-Carotene
Peak 4 : 9-cis β-Carotene

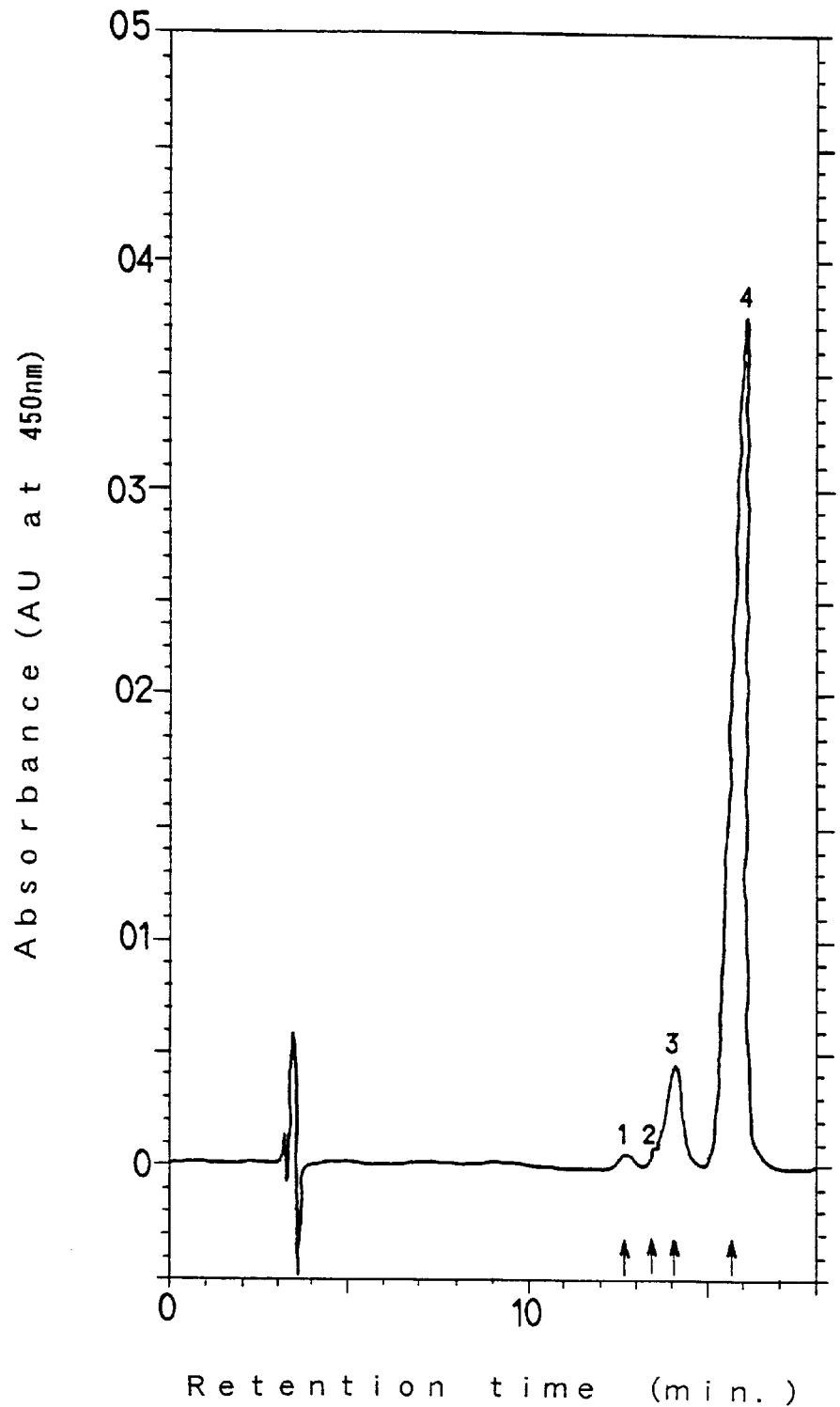
Peak 1 : α-Carotene
Peak 2 : Unknown carotene
Peak 3 : All-trans β-Carotene
Peak 4 : 9-cis β-Carotene

METHOD OF OBTAINING A COMPOSITION CONTAINING 9-CIS β-CAROTENE IN HIGH-PURITY

BACKGROUND OF THE INVENTION

1. Field of the Invention

The present invention relates to a composition containing 9-cis β-carotene in high-purity and a method of obtaining the same.

2. Related Arts

β-Carotene is one of carotenoids contained in various colored vegetables and so on and has been well known as a substance which changes to vitamin A in vivo to show high biological activity. Further, β-carotene has been highly expected as one of ingredients for medicines, since it shows an anti-tumor activity and has an ability of eliminating active oxygen.

Natural β-carotene is mainly of all-trans type but various geometrical isomers thereof present, and in recent years, activities of the isomers have been greatly interested, since such isomers have been detected in human tissue, in addition to all-trans β-carotene.

Especially, 9-cis β-carotene becomes a center of such an attention, among the isomers. Since 9-cis β-carotene has been produced and accumulated in relatively large amount in green algae belonging to microalgae, Dunaliella, so that extractions of the substance from such a source have been tried [U.S. Pat. No. 5,310,554; U.S. Pat. No. 5,612,485; and Yuan et al., "Yaowu Shengwu Jishu", Vol. 3, pages 34–39 (1996) and so on].

However, almost all of the conventional methods of obtaining the composition containing 9-cis β-carotene utilize column chromatography and thus are not suitable for industrial scale production of the composition. The inventors have also tried to extract 9-cis β-carotene from *Dunaliella bardawil* by using hexane and obtained a solid composition containing 9-cis β-carotene, but content of 9-cis β-carotene therein remarkably varies in each experiment, so that they applied many complicated procedures including column chromatography to obtain fine needle-shaped 9-cis β-carotene as follows: removing the solid materials in hexane to obtain a filtrate, subjecting the filtrate to a silica gel chromatography, concentrating a carotene-rich fraction to obtain foamy solids, sonicating the solids in ethanol to obtain orange particles, dissolving the particles into chloroform, subjecting the resulting solution to ODS open column chromatography, concentrating a carotene-rich fraction to obtain an orange powder, subjecting the powder to preparative high-performance liquid chromatography (HPLC), and then concentrating the HPLC fraction which contains 9-cis β-carotene to cause precipitation thereof as the crystals [Suzuki et al., "Biochem. Mol. Biol. Int.", Vol. 39, pages 1077–1084 (1996)].

Methods of obtaining 9-cis β-carotene utilizing no column chromatography have also been proposed, but all of reports on such proposals have so referred to that a composition obtained is oily substance, in spite of that 9-cis β-carotene, inherently, is a solid substance having melting point of 122–123° C. [Polgar et al., "J. Amer. Chem. Soc.", Vol. 64, pages 1856–1861 (1942)]. This means that each of the compositions contains impurities other than 9-cis β-carotene, in some extent. In such a report, it has oftenly been described that "high-purity 9-cis β-carotene" was obtained by referring to its ratio to total carotene, but this report has some doubt in that impurities other than carotenes have not been taken into consideration and this becomes a great problem in case of that the composition shall be actually used as an ingredient for medicines.

SUMMARY OF THE INVENTION

An object of the invention, therefore, is to provide a composition containing 9-cis β-carotene, which is not only high in ratio of 9-cis β-carotene to total carotene, but also small in amount of impurities other than carotenes and which can be said as "high-purity 9-cis β-carotene" in inherent meaning.

Another object of the invention is to provide a method of obtaining the composition, which is applicable to an industrial scale production thereof.

The inventors have energetically studied and investigated to find that a powdery or crystalline composition containing 9-cis β-carotene can be obtained by washing with ethanol dry powder of an alga belonging to Dunaliella, and then treating with hexane in stepwise, and that an analysis of the composition shows a high percentage of 9-cis β-carotene. The procedures are similar to those disclosed in said literature of "Biochem. Mol. Biol. Int.", Vol. 39, pages 1077–1084 (1996), but greatly different in that in the method of the literature, the final treatment by hexane is carried out to cause precipitation of remaining all-trans β-carotene, but in the method according to the invention, the treatment is carried out to cause precipitation of not all-trans β-carotene but 9-cis β-carotene.

A method of obtaining the composition containing 9-cis β-carotene in high-purity and according to the invention comprises a first step consisting essentially of washing with ethanol dry powder of an alga belonging to Dunaliella, adding hexane to stir the same, subjecting to filtration, and concentrating a filtrate to obtain a semi-solid concentrate; a second step consisting essentially of adding hexane to said semi-solidic concentrate in an amount ratio of 10–18 ml of hexane to 1 g of said semi-solid concentrate to stir the same, subjecting to filtration, and concentrating a filtrate to obtain an oily concentrate; and a third step consisting essentially of adding hexane to said oily concentrate in an amount ratio of 2–4.5 ml of hexane to 1 g of said oily concentrate to dissolve the same, leaving the solution, as it is, to cause a separation of solids, obtaining, washing, and drying the solids. The composition according to the invention and to be obtained by such a method is characterized by a rubiginous powder or crystals containing 9-cis β-carotene in an amount of 75% or more to total amount of the composition.

As a raw material for carrying out the invention, a micro green alga belonging to Dunaliella is used. Since it has been known that the algae belonging to Dunaliella produce 9-cis β-carotene in a large amount to accumulate the same therein and more particularly, 9-cis β-carotene has been accumulated in a large amount in *Dunaliella bardawil* and *Dunaliella salina*, it is preferable to select these algae. For instance, *Dunaliella bardawil* usually contains 9-cis β-carotene and all-trans β-carotene in a ratio of about 1:1.

The first step of the method according to the invention is procedures for washing the alga and extracting carotenes. Firstly, ethanol is added to dry powder of the alga to stir the same to dissolve ethanol-soluble substances as much as possible and remove the substances by filtration. The stirring operation may be carried out at room temperature and there is no special limitation in amount of ethanol to be added and stirring period of time. No substantial loss of 9-cis β-carotene shall cause in this washing treatment, since solubility of β-carotenes to ethanol is quite low.

The washing operation by ethanol is very important. Because impurities and carotenes interact with each other in an adsorptional manner, when the impurities are not sufficiently removed through this washing treatment, the composition containing 9-cis β-carotene cannot finally be obtained as solids. Therefore, it is preferable to carry out the washing operation repeatedly.

After obtained ethanol-insoluble substance by filtration, hexane is added thereto and stirred to cause elution of carotenes. The carotene containing solution was filtered and a filtrate is concentrated to obtain a semi-solid substance (hereinafter referred to as "concentrate A").

The second step is procedures for separating and removing all-trans β-carotene from the concentrate A obtained by the first step. The procedures utilize a difference in solubility of 9-cis β-carotene and all-trans β-carotene to hexane, namely the solubility of the former is 2 g/100 ml (24° C.) and the latter is 0.11 g/100 ml (30° C.), to cause separation of all-trans β-carotene for removing the same.

In connection with the procedures, it is necessary to grasp content of each carotene in the concentrate A, and the contents can be measured by HPLC. By this measurement, an optimum amount of hexane to be added to the concentrate A can be calculated from solubility of the carotenes to hexane and the carotene contents in the concentrate A. However, the solubility of 9-cis β-carotene and all-trans β-carotene is greatly influenced by impurities in the concentrate A and thus there are many cases of that an actual optimum amount of hexane to be added for separating all-trans β-carotene from 9-cis β-carotene does not coincide with the calculated amount.

Therefore, the inventors have energetically studied and investigated the matter to find that it is suitable to add hexane in an amount of 10–18 ml to 1 g of the concentrate A, as stated before. Thus, hexane is added to the concentrate A in such an amount ratio to stir the same for causing separation or precipitation of all-trans β-carotene which is removed by, for instance, filtration.

In case of that an amount of hexane to be added to the concentrate A is less than said range, namely the amount is less than 10 ml to 1 g of the concentrate A, 9-cis β-carotene is apt to be precipitated together with all-trans β-carotene to cause loss of the former. In case of that an amount of hexane is more than 18 ml to 1 g of the concentrate A, while, an amount of all-trans β-carotene remaining in hexane increases, which makes difficult to obtain a final composition containing 9-cis β-carotene in high-purity.

The stirring operation may be carried out at room temperature, but it is preferable to select lower temperature condition, for instance, the temperature of about 0° C. for separating all-trans β-carotene with good efficiency.

Thereafter, all-trans β-carotene is separated by, for instance, filtration and a filtrate is concentrated to obtain viscous oily substance (hereinafter referred to as "concentrate B").

The third step is procedures for separating from the concentrate B the composition containing 9-cis β-carotene, as solids. The composition can be separated by adding hexane to the concentrate B obtained by the second step, stirring the same and then leaving it as it is. The separated solids are collected by filtration, washed with ethanol and then dried to give the desired composition containing 9-cis β-carotene in high-purity, in the form of powder or fine crystals.

In the concentrate B obtained by the second step, there are some impurities other than the carotenes. The impurities at this stage easily dissolve into hexane and thus, for separating 9-cis β-carotene, it is preferable to use hexane in an amount as small as possible.

The inventors have studied as to an optimum amount of hexane for separating the composition containing 9-cis β-carotene to find that a suitable amount of hexane is 2–4.5 ml to 1 g of the concentrate B, as stated before. Namely, when hexane is added to the concentrate B in such a ratio to dissolve the same and leaving the solution as it is, the composition containing 9-cis β-carotene separates, as solids.

In case of that an amount of hexane to be added to the concentrate B is less than said range, namely the amount is less than 2 ml to 1 g of the concentrate B, the interactions of 9-cis β-carotene with the impurities make difficult to separate 9-cis β-carotene, as solids and even if the separation of 9-cis β-carotene is possible, the impurities are apt to be taken into the separated solids to make lower purity of the final composition. In case of that an amount of hexane is more than 4.5 ml to 1 g of the concentrate B, while, an amount of 9-cis β-carotene remaining in hexane increases to cause a decrease in yield of the desired composition.

The operation may be carried out at room temperature, but it is preferable to select lower temperature condition, for instance, the temperature of about −20° C. for separating 9-cis β-carotene with good efficiency.

The separated solids are collected by filtration, washed with ethanol and then dried to afford the desired composition containing 9-cis β-carotene in high-purity, in the form of powder or fine crystals.

The resulting composition contains 9-cis β-carotene in an amount of 80% or more to total carotene and 75% or more to total amount containing impurities.

BRIEF DESCRIPTION OF THE DRAWING

The figure is a chromatogram showing results of HPLC made on a composition containing 9-cis β-carotene, which was obtained by the method according to the invention.

DETAILED DESCRIPTION OF PREFERRED EMBODIMENT

The invention will now be further explained with reference to a Production Example and Test Example.

Example (Production of composition containing 9-cis β-carotene)

To dry powder of *Dunaliella bardawil* (2000 g), was added ethanol (8000 ml), stirred for 15 minutes at room temperature, and then filtered. To solids obtained by the filtration, was added again ethanol (8000 ml), stirred for 15 minutes at room temperature, and then filtered to obtain washed algal powder. To the washed powder, was added hexane (18000 ml), stirred for 30 minutes at room temperature, and then filtered to obtain a filtrate. The filtrate was concentrated to obtain a blackish brown semi-solidic substance (98.46 g). To the semi-solidic substance, was added hexane (1477 ml, corresponding to 15 ml to 1 g of the semi-solidic substance), stirred for one hour at 0° C., and then filtered to obtain a filtrate. The filtrate was concentrated to obtain a viscous oily substance (59.59 g) which has a glossy and blackish brown color. To the oily concentrate, was added hexane (209 ml, corresponding to 3.5 ml to 1 g of the oily concentrate) to immediately dissolve the same, and then left to stand over one night at −20° C. Separated solids were collected by filtration, washed with ethanol, and dried to obtain 31.66 g of a desired composition containing 9-cis β-carotene in high-purity, as rubiginous powder.

Test Example (HPLC analysis)

The composition obtained by said Example was subjected to HPLC. Analytical conditions therefor were as follows.

Detector : Detector with a photodiode array (Type MCPD-3600 manufactured by Tosoh Corp.), Detection wave-length : 450 nm, Guard column : TSK guardgel ODS-120A (3.2 mm i.d.× 15 mm, manufactured by Tosoh Corp.), Analytical column : Vydac 201TP54 (4.6mm i.d.×250 mm, manufactured by The Separations Group, Hesperia, Calif.), Column temperature : 27±0.1° C., and Mobile phase : Mixture of methanol and chloroform (95:5, V/V) containing 10 mM ammonium acetate, Flow rate : 1 ml/min.

A chromatogram under such analytical conditions is shown in the figure. Calculation of ratio of 9-cis β-carotene to total carotene based on the analytical results showed as 86.8% to find that the composition obtained by the invention contains 9-cis β-carotene in high-purity.

It was found that a peak area of 9-cis β-carotene part in this analysis (measured value, namely AU×Δ min) is 0.0190. A purified 9-cis β-carotene was obtained by refining and isolating the same through HPLC and then subjecting to crystallization. The purified 9-cis β-carotene in the form of needle crystals was analyzed under conditions as given above to show that a peak area is 0.0225. Therefore, it has been found that content of 9-cis β-carotene in the total amount of the composition according to the invention is 84.4%.

What is claimed is:

1. A method of obtaining a composition containing 9-cis-β-carotene, which consists essentially of a first step of washing a dry powder of alga belonging to Dunaliella with ethanol, adding hexane to stir the washed alga, subjecting to filtration, and concentrating a filtrate to obtain a semi-solid concentrate; a second step of adding hexane to said semi-solid concentrate in an amount ratio of 10–18 ml of hexane to 1 g of said semi-solid concentrate to stir the mixture of hexane and said semi-solid concentrate, subjecting the mixture to filtration, and concentrating a filtrate to obtain an oily concentrate; and a third step of adding hexane to said oily concentrate in an amount ratio of 2–4.5 ml of hexane to 1 g of said oily concentrate to dissolve said oily concentrate, leaving the solution, as it is, to cause a separation of solids, subjecting to filtration to obtain solids, washing the solids with ethanol, and drying the washed solids, wherein said solids contain 9-cis-β-carotene in an amount of at least 75% based on the total amount of said solids.

2. A method of obtaining a composition as claimed in claim 1, wherein said alga belonging to Dunaliela is selected from the group consisting of *Dunaliela salina* and *Dunaliela bardawil*.

3. A method of obtaining a composition as claimed in claim 1, wherein the stirring operation in said second step is carried out at a temperature lower than room temperature.

4. A method of obtaining a composition as claimed in claim 3, wherein said stirring operation is carried out at 0° C.

5. A method of obtaining a composition as claimed in claim 1, wherein the leaving of solution in said third step is carried out at a temperature lower than room temperature.

6. A method of obtaining a composition as claimed in claim 5, wherein the leaving temperature of said solution is −20° C.

* * * * *